(12) United States Patent
Pazenok et al.

(10) Patent No.: US 8,586,753 B2
(45) Date of Patent: *Nov. 19, 2013

(54) PROCESS FOR THE PREPARATION OF 1-ALKYL AND 1-ARYL-5-PYRAZOLECARBOXYLIC ACID DERIVATIVES

(75) Inventors: Sergii Pazenok, Solingen (DE); Norbert Lui, Odenthal (DE); Igor Gerus, Kiew (UA)

(73) Assignee: Bayer CropScience AG, Monheim (DE)

( * ) Notice: Subject to any disclaimer, the term of this patent is extended or adjusted under 35 U.S.C. 154(b) by 134 days.

This patent is subject to a terminal disclaimer.

(21) Appl. No.: 12/969,145

(22) Filed: Dec. 15, 2010

(65) Prior Publication Data

US 2011/0152532 A1     Jun. 23, 2011

(30) Foreign Application Priority Data

Dec. 15, 2009  (EP) .................................... 09179299

(51) Int. Cl.
*C07D 401/04*       (2006.01)
*C07D 231/14*       (2006.01)

(52) U.S. Cl.
USPC ..................................... 546/275.4; 548/374.1

(58) Field of Classification Search
USPC ..................................... 546/275.4; 548/374.1
See application file for complete search history.

(56) References Cited

U.S. PATENT DOCUMENTS

| 8,222,435 B2 * | 7/2012 | Pazenok et al. .............. 549/377 |
| 2010/0029478 A1 | 2/2010 | Alig et al. |
| 2011/0087029 A1 | 4/2011 | Pazenok et al. |

FOREIGN PATENT DOCUMENTS

| WO | WO 03/016282 A2 | 2/2003 |
| WO | WO 2005/049578 A1 | 6/2005 |
| WO | WO 2007/144100 A1 | 12/2007 |
| WO | WO 2010/112178 A1 | 10/2010 |

OTHER PUBLICATIONS

Adamo, M.F.A., et al., "Practical routes to diacetylenic ketones and their application for preparation of alkynyl substituted pyridines, pyrimidines and pyrazoles," *Tetrahedron* 59:2197-2205, Elsevier Science Ltd., England (2003).
Bishop, B.C., et al., "Regioselective Synthesis of 1,3,5-Substitute Pyrazoles from Acetylenic Ketones and Hydrazines," *Synthesis* 2004(I):0043-0052, Georg Thieme Verlag, Germany (2004).
Liang, J.T., et al., "Design of Concise, Scalable Route to a Cholecystokinin 1 (CCK 1) Receptor Antagonist," *J. Org. Chem.* 72:8243-8250, American Chemical Society, United States (2007).
Martins, M.A.P., et al., "Synthesis of new halo-containing acetylenes and their application to the synthesis of azoles," *Tetrahedron Lett.* 45:4935-4938, Elsevier Ltd. England (2004).
International Search Report for International Patent Application No. PCT/EP2010/069385, European Patent Office, Rijswijk, Netherlands, mailed on Jan. 1, 2011, 2 pages.

* cited by examiner

*Primary Examiner* — Patricia L Morris
(74) *Attorney, Agent, or Firm* — Sterne, Kessler, Goldstein & Fox P.L.L.C.

(57) ABSTRACT

The present invention relates to a process for the preparation of 1-alkyl- or 1-aryl-substituted 5-pyrazolecarboxylic acid derivatives comprising the reaction of substituted 1,3-dioxolanes and 1,4-dioxanes with alkyl- or arylhydrazines to give 1-alkyl- or 1-aryl-substituted dihydro-1H-pyrazoles, and their further reaction to give 1-alkyl- or 1-aryl-substituted 5-pyrazolecarboxylic acid derivatives, which can be used as valuable intermediates for producing insecticidally effective anthranilamides.

15 Claims, No Drawings

PROCESS FOR THE PREPARATION OF 1-ALKYL AND 1-ARYL-5-PYRAZOLECARBOXYLIC ACID DERIVATIVES

The present invention relates to a process for the preparation of 1-alkyl- or 1-aryl-substituted 5-pyrazolecarboxylic acid derivatives comprising the reaction of substituted 1,3-dioxolanes and 1,4-dioxanes with alkyl or arylhydrazines to give 1-alkyl- or 1-aryl-substituted dihydro-1H-pyrazoles, their further reaction with the elimination of water to give 1-alkyl- or 1-aryl-substituted pyrazoles and their further processing to give 5-pyrazolecarboxylic acid derivatives.

1-alkyl-/1-aryl-substituted pyrazoles and 1H-pyrazoles are valuable intermediates for producing anthranilamides, which can be used as insecticides.

The literature already describes that pyrazoles can be formed by reacting 1,3-dicarbonyls or corresponding 1,3-bis-electrophilic reagents with monoalkyl- or monoarylhydrazines (Synthesis 2004, N1. pp 43-52). However, it is reported that in the case of monoalkyl- or monoarylhydrazines, a mixture of regioisomeric pyrazoles results (Tetrahedron 59 (2003), 2197-2205; Martins et al., T. L. 45 (2004) 4935). Attempts to exclusively obtain a regioisomer have failed (JOC 2007, 72, 8243-8250). The literature likewise describes a process for the preparation of trifluoromethylpyrazoles (WO 2003/016282). Likewise described are preparation processes of (het)aryl-substituted pyrazoles (WO 2007/144100), in which the corresponding pyrazoles are obtained by reducing diesters with DIBAL or LiAlH$_4$. However, very low temperatures are required for this, and the use of DIBAL is uneconomic. WO 2010/112178 describes the preparation of 5-pyrazolecarboxylic acid derivatives by cyclization of acetylene ketones, with the synthesis of acetylene ketones requiring BuLi and very low temperatures (−70° C. to −80° C.).

The object of the present invention is therefore to provide novel, economical processes for the preparation of 1-alkyl-/1-aryl-substituted 5-pyrazolecarboxylic acid derivatives which carry a further substituent (CH$_2$—R$^2$) in the pyrazole ring in the 3-position. The process should not have the disadvantages described above and should be characterized by a process control which can be carried out particularly well and easily even on an industrial scale.

The object was achieved according to the present invention by a process for the preparation of 1-allyl-/1-aryl-substituted 5-pyrazolecarboxylic acid derivatives of the general formula (I)

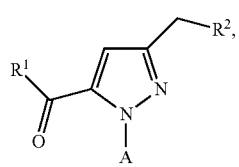

in which
R$^1$ is hydroxy, halogen, alkoxy, aryloxy,
R$^1$ is preferably hydroxy, halogen, (C$_1$-C$_6$)alkoxy,
R$^1$ is particularly preferably hydroxy, halogen, (C$_1$-C$_4$)alkoxy,
R$^2$ is hydroxy, alkoxy, arylalkoxy, halogen, O—(C=O)alkyl, O—(C=O)O-alkyl, O(C=O)haloalkyl, OSO$_2$alkyl, OSO$_2$¯haloalkyl, OSO$_2$-aryl,
R$^2$ is preferably hydroxy, halogen, O—(C=O)(C$_1$-C$_6$)alkyl, OSO$_2$(C$_1$-C$_6$)alkyl, OSO$_2$¯halo(C$_1$-C$_6$)alkyl,
R$^2$ is particularly preferably hydroxy, halogen, O—(C=O)CH$_3$,
A is alkyl or
is the group

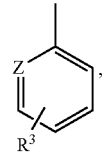

A is preferably (C$_1$-C$_4$)alkyl or
is the group

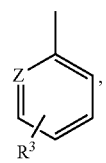

A is particularly preferably the group

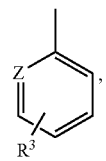

R$^3$ is halogen, CN, NO$_2$, alkyl, cycloalkyl, haloalkyl, halocycloalkyl, alkoxy, haloalkoxy, alkylamino, dialkylamino, cycloalkylamino,
R$^3$ is preferably halogen, CN, NO$_2$, (C$_1$-C$_6$)-alkyl, halo(C$_1$-C$_6$)-alkyl, (C$_1$-C$_6$)alkoxy, halo(C$_1$-C$_6$)alkoxy,
R$^3$ is particularly preferably F, chlorine, bromine, iodine, CN, (C$_1$-C$_4$)-alkyl, halo(C$_1$-C$_4$)-alkyl, or halo(C$_1$-C$_4$)alkoxy,
R$^3$ is very particularly preferably fluorine, chlorine, bromine or iodine,
R$^3$ is particularly preferably chlorine,
Z is CH, N,
Z is preferably and particularly preferably N,
characterized in that substituted 1,3-dioxolanes and 1,4-dioxanes of the formula (II)

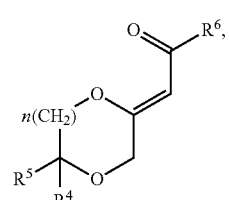

in which
R$^4$, R$^5$ independently of one another are hydrogen, alkyl, aryl, arylalkyl, alkoxy,
R$^4$, R$^5$ can furthermore form a 4-, 5-, 6- or 7-membered, saturated, optionally substituted ring which can contain 1-2 heteroatoms from the series N, S, O, $R^6$ is trihalomethyl, (C=O)Oalkyl, (C=O)Ohaloalkyl,
n is 0 or 1,
n is preferably and particularly preferably 0,
   with alkyl- or arylhydrazines of the formula (III)

$$A\text{-}NHNH_2 \quad (III),$$

in which A is alkyl or is the group

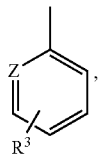

$R^3$ is halogen, CN, $NO_2$, alkyl, cycloalkyl, haloalkyl, halocycloalkyl, alkoxy, haloalkoxy, alkylamino, dialkylamino, cycloalkylamino,
Z is CH, N,
are converted to 1-alkyl-/1-aryl-substituted dihydro-1H-pyrazoles of the formula (IV),

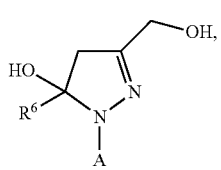

in which $R^6$, A have the meanings given above,
these are further converted, optionally without prior isolation with the elimination of water, to 1-alkyl-/1-aryl-substituted pyrazoles of the formula (V)

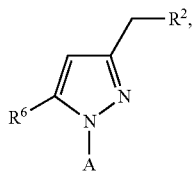

in which $R^2$, $R^6$ and A have the meanings given above,
these compounds of the general formula (V)
are converted to pyrazolecarboxylic acid derivatives of the formula (I),

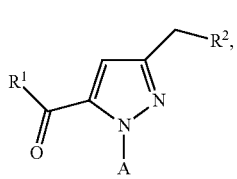

in which $R^1$, $R^2$ and A have the meanings given above.

In particular, the process according to the invention is characterized by a very short synthesis route, high regioselectivity during the formation of the pyrazole ring, favourable raw materials, such as, for example, 2,2-dimethyl-4-methylene-1,3-dioxolane, 4-methylene-1,3-dioxolane, acid chlorides and alkyl- or arylhydrazines, and also by a process control that can be carried out particularly well and easily even on an industrial scale.

The process according to the invention can be explained by reference to the following scheme (I):

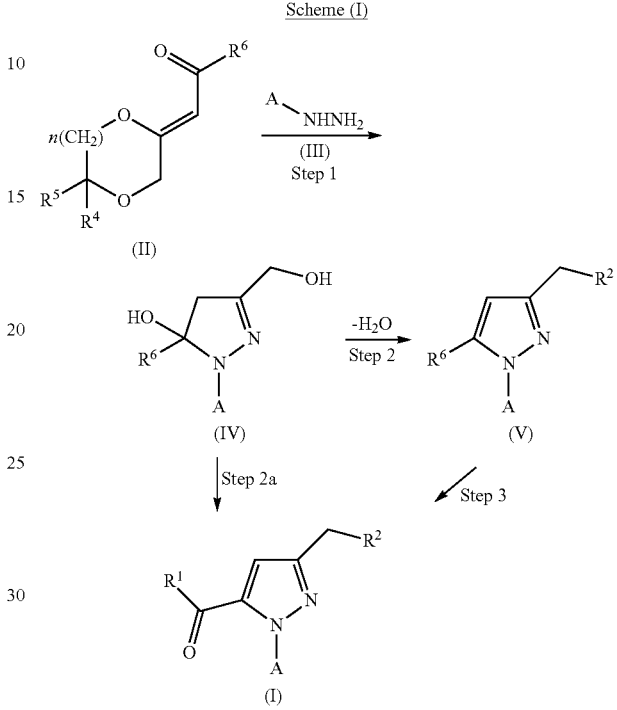

where $R^1$, $R^2$, $R^4$, $R^5$, $R^6$, A, n have the meanings given above.

The compounds of the formula (IV) in which $R^6$ is (C=O) Oalkyl can also be converted in step (2a) directly into compounds of the formula (I) in which $R^1$ is Oalkyl and $R^2$ is hydroxy, halogen, O—(C=O)($C_1$-$C_6$)alkyl, $OSO_2$($C_1$-$C_6$) alkyl, $OSO_2$halogen($C_1$-$C_6$)alkyl.

In a further embodiment of the process, compounds of the formula (II)

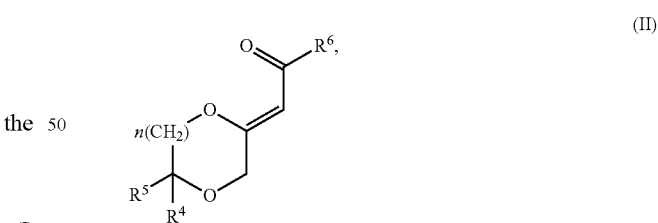

in which n is 0 and $R^4$, $R^5$ and $R^6$ have the definitions stated above,
are reacted first with nucleophiles of the formula (VI)

$$H_2L \quad (VI),$$

in which
L is O, NH or $NR^7$,
$R^7$ is alkyl,
to give aminohydroxyoxopentenoates or hydroxy-2,4-dioxopentanoates of the formula (VII), which may be present in the form of two tautomeric foams (VIIa) and (VIIb) and may form a ring of the formula (VIIc), (VIId),

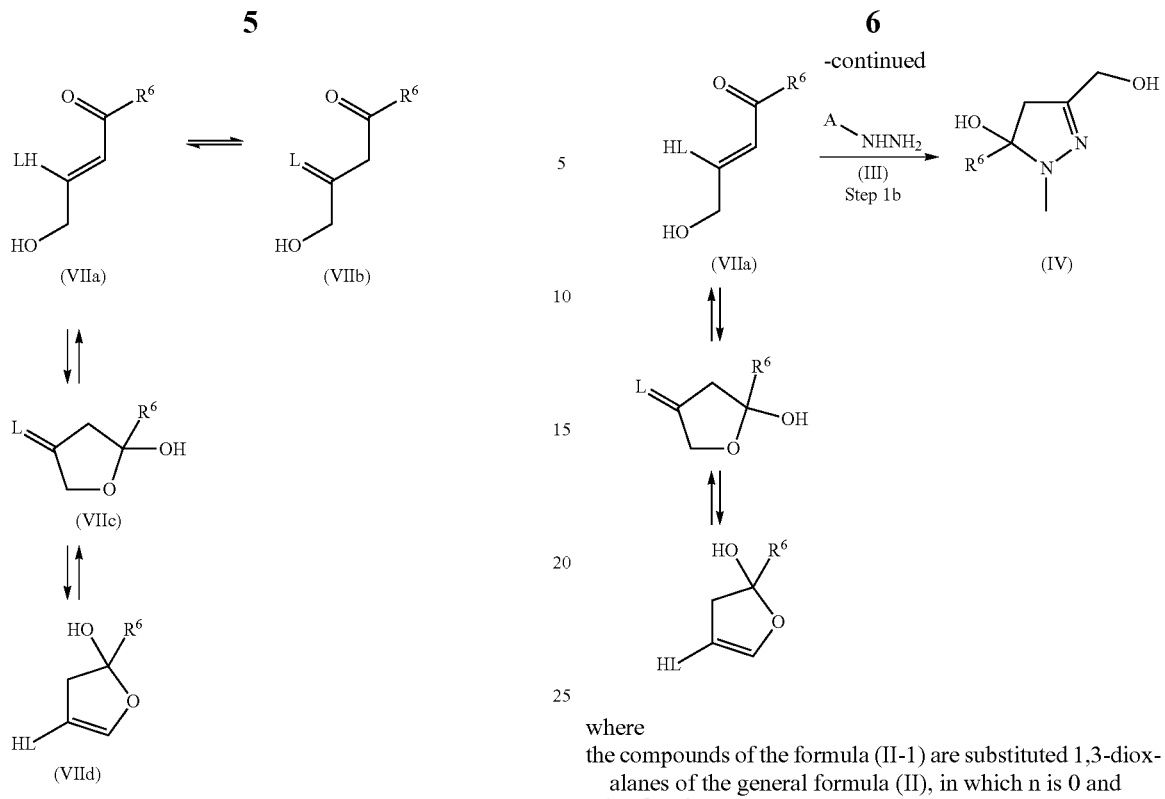

which are subsequently reacted with arylhydrazines of the formula (III)

A-NHNH$_2$            (III), in which A has the definitions indicated above,
to give 1-alkyl-/1-aryl-substituted dihydro-1H-pyrazoles of the formula (IV)

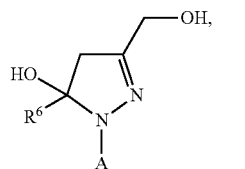

in which A and R$^6$ have the definitions indicated above. These compounds can be reacted further as indicated above to give compounds of the general formula (I).

This embodiment of the process according to the invention can be illustrated by the following scheme (IA)

Scheme (IA)

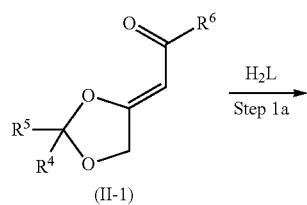

where
the compounds of the formula (II-1) are substituted 1,3-dioxalanes of the general formula (II), in which n is 0 and R$^4$, R$^5$, R$^6$, A and L have the general definitions indicated above.

General Definitions

In connection with the present invention, unless defined otherwise, the term halogens (X) includes those elements which are selected from the group consisting of fluorine, chlorine, bromine and iodine, with fluorine, chlorine and bromine being preferably used and fluorine and chlorine being particularly preferably used. Substituted groups may be mono- or polysubstituted, where, in the case of multiple substitutions, the substituents may be identical or different.

Alkyl groups substituted with one or more halogen atoms (—X)=(haloalkyl groups) are selected for example from trifluoromethyl (CF$_3$), difluoromethyl (CHF$_2$), CCl$_3$, CFCl$_2$, CF$_3$CH$_2$, ClCH$_2$, CF$_3$CCl$_2$.

Alkyl groups in connection with the present invention, unless defined otherwise, are linear or branched hydrocarbon groups.

The definition of alkyl and C$_1$-C$_{12}$-alkyl includes for example the meanings methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

Cycloalkyl groups in connection with the present invention are, unless defined otherwise, ring-shaped saturated hydrocarbon groups.

Aryl radicals in connection with the present invention are, unless defined otherwise, aromatic hydrocarbon radicals which can have one, two or more heteroatoms which are selected from O, N, P and S and can optionally be substituted by further groups.

Arylalkyl groups and arylalkoxy groups in connection with the present invention are, unless defined otherwise, aryl-group-substituted alkyl or alkoxy groups, respectively, which may have an alkylene chain. Specifically, the definition of arylalkyl includes for example the meanings benzyl- and phenylethyl-; the definition of arylalkoxy includes for example the meaning benzyloxy.

Alkylaryl groups (alkaryl groups) and alkylaryloxy groups in connection with the present invention are, unless defined otherwise, alkyl-group-substituted aryl groups or aryloxy groups, respectively, which can have a $C_{1-8}$-alkylene chain and can have one or more heteroatoms selected from O, N, P and S in the aryl backbone or aryloxy backbone.

The compounds according to the invention may optionally be present as mixtures of different possible isomeric forms, in particular stereoisomers, such as e.g. E- and Z-, threo- and erythro-, and also optical isomers, but optionally also tautomers. Both the E- and also the Z-isomers, and also the threo- and erythro-, as well as the optical isomers, any desired mixtures of these isomers, and also the possible tautomeric forms are disclosed and claimed.

Substituted 1,3-dioxolanes and 1,4-dioxanes of the Formula (II)

The substituted 1,3-dioxolanes and 1,4-dioxanes used as starting materials when carrying out the process according to the invention are generally defined by the formula (II),

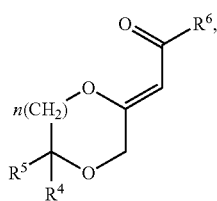

(II)

where
$R^4$ and $R^5$ independently of one another are hydrogen, alkyl, arylalkyl, aryl or alkoxy,
$R^4$, $R^5$ can furthermore form a 4-, 5- or 6-membered, saturated, optionally substituted ring which can contain 1-2 heteroatoms from the series N, S, O,
$R^4$ and $R^5$ independently of one another are preferably hydrogen or $(C_1-C_{12})$alkyl,
$R^4$ and $R^5$ independently of one another are particularly preferably hydrogen or methyl;
n is 0 or 1,
n is preferably and particularly preferably 0.
$R^6$ is trihalomethyl, (C=O)Oalkyl, (C=O)Ohaloalkyl,
$R^6$ is preferably trichloromethyl, (C=O)O($C_1-C_6$)alkyl,
$R^6$ is particularly preferably trichloromethyl, (C=O)Omethyl and (C=O)Oethyl.

Examples of dioxolane derivatives of the formula (II) suitable according to the invention are 1,1,1-trichloro-3-(2,2-dimethyl-1,3-dioxolan-4-ylidene)acetone, 1,1,1-trifluoro-3-(2,2-dimethyl-1,3-dioxolan-4-ylidene)acetone, methyl 3-(2,2-dimethyl-1,3-dioxolan-4-ylidene)-2-oxopropanoate, methyl 3-(1,3-dioxolan-4-ylidene)-2-oxopropanoate, ethyl 3-(2,2-dimethyl-1,3-dioxolan-4-ylidene)-2-oxopropanoate or ethyl 3-(5,5-dimethyl-1,4-dioxan-2-ylidene)-2-oxopropanoate.

The compounds of the formula (II) are novel and can be prepared by reacting compounds of the general formula (II-a),

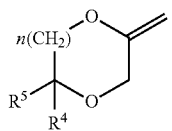

(II-a)

in which $R^4$, $R^5$ have the meanings given above, with anhydrides or acid chlorides with the general formula (II-b)

(II-b)

in which R is halogen or —O(C=O)$R^6$ and $R^6$ has the meanings given above,
in the presence of a base (cf. Scheme (II)), Scheme (II)

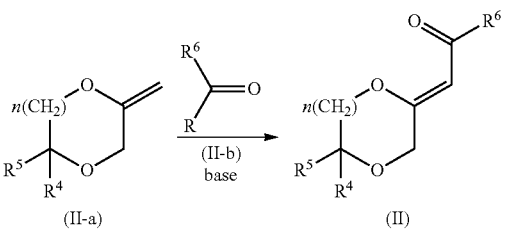

where
$R^4$, $R^5$ and $R^6$ have the meanings given above and R is halogen or —O(C=O)$R^6$.

Alkyl- and Arylhydrazines of the General Formula (III)

The alkyl- and arylhydrazines used according to the present invention are compounds of the general formula (III)

A-NHNH$_2$ (III), in which
A is alkyl or
is the group

A is preferably $(C_1-C_4)$alkyl or
is the group

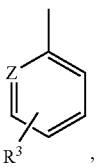

A is particularly preferably the group

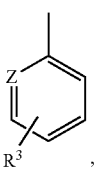

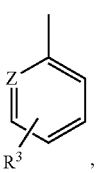

$R^3$ is halogen, CN, NO$_2$, alkyl, cycloalkyl, haloalkyl, halocycloalkyl, alkoxy, haloalkoxy, alkylamino, dialkylamino, cycloalkylamino, $R^3$ is preferably halogen, CN, $NO_2$, $(C_1\text{-}C_6)$-alkyl, halo($C_1$-$C_6$)-alkyl, $(C_1\text{-}C_6)$alkoxy, halo($C_1\text{-}C_6$)alkoxy, $R^3$ is particularly preferably F, chlorine, bromine, iodine, CN, $(C_1\text{-}C_4)$-alkyl, halo($C_1\text{-}C_4$)-alkyl or halo($C_1\text{-}C_4$)alkoxy, $R^3$ is very particularly preferably fluorine, chlorine, bromine or iodine, $R^3$ is especially preferably chlorine, Z is CH, N, Z is preferably and particularly preferably N.

Examples of hydrazines suitable according to the invention are methylhydrazine, ethylhydrazine, 3-chloro-2-hydrazinopyridine, phenylhydrazine, o- and p-chlorophenylhydrazine, o- and p-methylphenylhydrazine, nitrophenylhydrazines. These compounds are commercially available.

Step (1)

In a first embodiment of the present process, firstly substituted 1,3-dioxolanes or 1,4-dioxanes of the formula (II) are reacted with alkyl- or arylhydrazines of the formula (III)

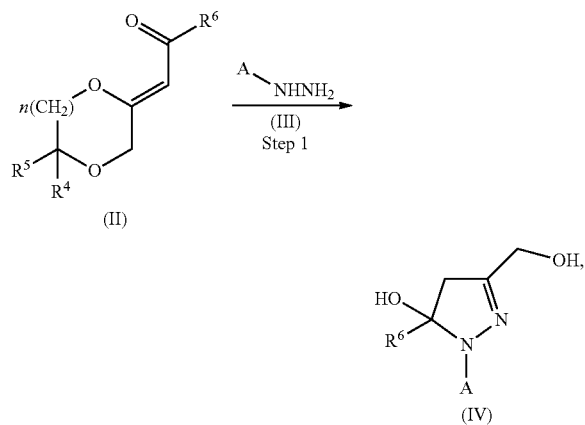

in which $R^4$, $R^5$ and $R^6$ have the meanings given above.

Surprisingly, it has been found that the reaction of substituted 1,3-dioxolanes or 1,4-dioxanes of the formula (II) with alkyl- or arylhydrazines of the formula (III) takes place selectively to give 1-alkyl-/1-aryl-substituted dihydro-1H-pyrazoles of the formula (IV). The second possible regioisomer has not been observed. It is also considered surprising that, at the end of the reaction with dioxolanes of the formula (II-1), a small part (about below 3%) of the hydrazine of the general formula (III) has been converted, by reaction with ketone of the general formula (VIII) eliminated in the reaction, into hydrazone of the general formula (IX). Surprisingly, the hydrazone of the general formula (IX) reacts with dioxolanes of the formula (II-1) to give the compound of the formula (IV).

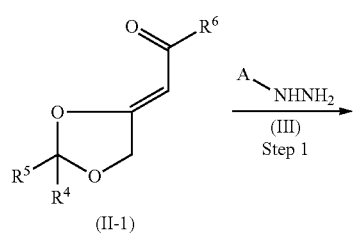

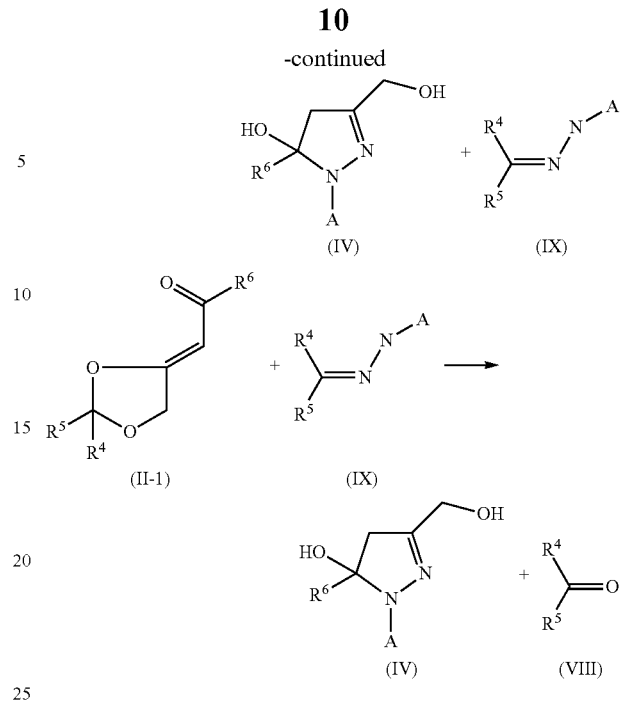

Process step (1) according to the invention is preferably carried out within a temperature range from $-20°$ C. to $+100°$ C., particularly preferably at temperatures of from $-10°$ C. to $+80°$ C., particularly preferably 20 to $60°$ C.

Process step (1) according to the invention is generally carried out under atmospheric pressure. Alternatively, however, it is also possible to work under reduced pressure in order to remove ketone formed in the process from the reaction mixture.

The reaction time is not critical and can be chosen in a range between a few and several hours depending on the substrate, on the batch size and temperature.

When carrying out the process step according to the invention, 1 mol of the substituted 1,3-dioxolane or 1,4-dioxane of the formula (II) is reacted with 0.8 mol to 2 mol, preferably 0.9 mol to 1.7 mol, particularly preferably with 1.0-1.2 mol of the alkyl- or arylhydrazine of the formula (III).

Suitable solvents are, for example, aliphatic, alicyclic or aromatic hydrocarbons, such as e.g. petroleum ether, n-hexane, n-heptane, cyclohexane, methylcyclohexane, benzene, toluene, xylene or decalin, and halogenated hydrocarbons, such as e.g. chlorobenzene, dichlorobenzene, dichloromethane, chloroform, tetrachloromethane, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisol; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphortriamide; sulfoxides, such as dimethyl sulfoxide or sulfones, such as sulfolane, alcohols such as methanol, ethanol, isopropanol. Particular preference is given to using toluene, ethanol, methyl tert-butyl ether, THF, isopropanol, acetonitrile.

Step (1a)

In a further embodiment of the present process, substituted 1,3-dioxolanes of the formula (II-1) are first reacted with nucleophiles of the formula (VI) (cf. scheme (IA)). This releases ketone of the general formula (VIII) and removes it before step 1b is carried out.

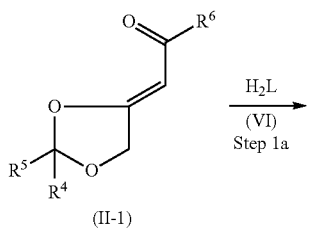 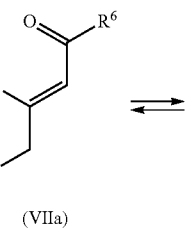 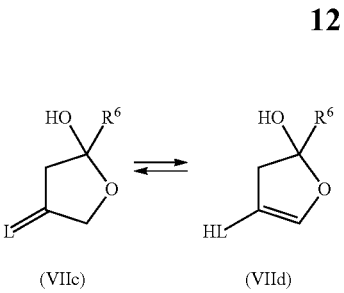

The compounds of the general formula (VII) are new.

They may be present in various tautomeric forms, as for example as hydroxyacetone derivatives, or may form a ring, in the form, for example, of cyclic 2-hydroxy-4-oxotetrahydrofuran. When this embodiment of the process according to the invention is carried out, the compounds of the general formula (VII) exhibit the same reactivity. Depending on the polarity and acidity of the solvent and on the temperature, different forms of the compounds of the general formula (VII) are present.

The implementation of process step (1a) according to the invention takes place preferably within a temperature range from −20° C. to +100° C., more preferably at temperatures from −10° C. to +80° C., more preferably at +20° C. to 60° C. Thus dioxolanes of the general formula (II-1) react with ammonia even at 0° C. within a few minutes to give the alkyl 4-amino-5-hydroxy-2-oxopent-3-enoates. For the reaction of dioxolanes of the formula (II-1) with water, in contrast, a number of hours at room temperature are needed.

Process step (1a) according to the invention is generally carried out under atmospheric pressure. It is particularly advantageous to operate under reduced pressure, in which case the ketone of the general formula (VIII) that is formed is removed from the mixture.

The reaction time is not critical and can be selected, depending on substrate, batch size and temperature, from a range between a few minutes and several hours.

When process step (1a) according to the invention is carried out, 1 mol of the substituted 1,3-dioxolane of the formula (II) is reacted with 0.8 mol to 2 mol, preferably 0.9 mol to 1.7 mol, more preferably with 1-1.3 mol, of the nucleophiles of the formula VI. It is possible to carry out the reaction in water, with the water serving as reagent and solvent.

The compounds of the formula (VIIa) are isolated by filtration, for example for solids such as methyl 4-amino-5-hydroxy-2-oxopent-3-enoates, or by extraction in the case of liquid intermediates.

It is also possible to react the compounds further without isolation.

Examples of suitable solvents include aliphatic, alicyclic or aromatic hydrocarbons, such as petroleum ether, n-hexane, n-heptane, cyclohexane, methylcyclohexane, benzene, toluene, xylene or decalin, for example, and halogenated hydrocarbons, such as chlorobenzene, dichlorobenzene, dichloromethane, chloroform, tetrachloromethane, dichloroethane or trichloroethane, for example, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoramide; sulphoxides, such as dimethyl sulphoxide or sulphones, such as sulpholane, alcohols such as methanol, ethanol and isopropanol, and water. Particular preference is given to using acetonitriles, isopropanol and water.

Step 1b

In this embodiment of the process according to the invention, the compounds of the formula (VII) formed in step 1a are reacted with alkyl- or arylhydrazines of the formula (III).

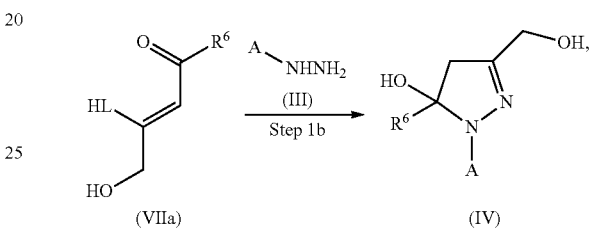

in which $R^4$, $R^5$, $R^6$, A and L have the definitions indicated above.

Surprisingly it has been found that the reaction of amino alcohols or alkyl 5-hydroxy-2,4-dioxopentanoates of the general formula (VII) with alkyl- or arylhydrazines of the formula (III) takes place selectively to form 1-alkyl-/1-aryl-substituted dihydro-1H-pyrazoles of the formula (IV).

Process step (1b) according to the invention is carried out preferably within a temperature range from −20° C. to +100° C., more preferably at temperatures from −10° C. to +80° C., very preferably at temperatures from +20° C. to +60° C.

Process step (1b) according to the invention is generally carried out under atmospheric pressure. Alternatively, however, it is also possible to operate under reduced pressure.

The reaction time is not critical and, depending on the batch size and temperature, may be selected in a range between a few and several hours.

When process step (1b) according to the invention is carried out, 1 mol of the compound of formula (VII) is reacted with 0.8 mol to 2 mol, preferably 0.9 mol to 1.7 mol, more preferably with 1 to 1.3 mol, of the alkyl- or arylhydrazine of formula (III).

The reaction can be accelerated by addition of acids. Suitable acids are HCl, $H_2SO_4$, $CF_3COOH$, trifluoromethanesulphonic acid, p-toluenesulphonic acid and methanesulphonic acid.

The acid is used in amounts of 0.2 to 2 mol, preferably 0.5 to 1.1 mol, based on the compound of the formula (VII).

Examples of suitable solvents are aliphatic, alicyclic or aromatic hydrocarbons, such as petroleum ether, n-hexane, n-heptane, cyclohexane, methylcyclohexane, benzene, toluene, xylene or decalin, for example, and halogenated hydrocarbons, such as chlorobenzene, dichlorobenzene, dichloromethane, chloroform, tetrachloromethane, dichloroethane or trichloroethane, for example, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoramide; sulphoxides, such as dimethyl sulphoxide or sulphones, such as sulpholane, alcohols such as methanol, ethanol and isopropanol. Particular preference is given to using toluene, ethanol, methyl tert-butyl ether, THF, isopropanol and acetonitrile.

The formed 1-alkyl-/1-aryl-substituted dihydro-1H-pyrazoles of the formula (IV) can be used without prior work-up in the subsequent step (2 or 2a) in which water elimination takes place.

Alternatively, the compounds of the formula (IV) can be isolated by suitable work-up steps and optionally further purification. Only at a later time can water then be eliminated.

Steps 2 and 2a. Aromatization Through Water Elimination

In one preferred embodiment of the process according to the invention, the compounds of the formula (IV) formed in step 1 are converted to 1-alkyl- or 1-aryl-substituted pyrazoles of the formula (V) with the elimination of water (cf. step 2 in scheme (I)).

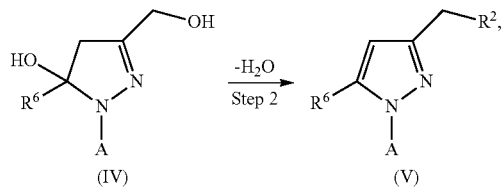

in which A, $R^2$, $R^6$ have the meanings given above.

For the elimination of water, the following reagents are suitable: HCl, $H_2SO_4$, $CF_3COOH$, trifluoromethanesulphonic acid, pivaloyl chloride, $PCl_5$, $POCl_3$, $P_4O_{10}$, polyphosphoric acid, $SOCl_2$, $(CH_3CO)_2O$, $(CF_3CO)_2O$, oxalyl chloride, methanesulphonic acid, p-toluenesulphonic acid, phosgene and diphosgene, methanesulphonyl chloride (MeSCl), $SiO_2$.

Preference is given to HCl, $(CF_3CO)_2O$, MeSCl, thionyl chloride, acetanhydride, oxalyl chloride, phosgene and $P_4O_{10}$.

During the elimination of water with anhydrides and haloanhydrides (e.g. $SOCl_2$, $POCl_3$, oxalyl chloride, phosgene, MeSCl), the derivatization of the $CH_2OH$ group also takes place, meaning that in just one step the compounds of the formula (V) in which $R^2$ is chlorine, bromine, fluorine, iodine, O—(C═O)alkyl, O—(C═O)O-alkyl, (C═O)haloalkyl, $OSO_2$alkyl, $OSO_2$-haloalkyl or $OSO_2$-aryl are obtained.

The reaction with acids such as HCl, $H_2SO_4$, $H_3PO_4$, polyphosphoric acid produces the compounds of the formula (V) in which $R^2$ is OH. If $R^6$ is (C═O)alkyl, it is advantageous to work with HCl in methanol in order to obtain the product of the formula (V) where $R^6$ is (C═O)Oalkyl and $R^2$ is OH in a high yield.

It is also possible to cleave off water through thermal stress (heating).

Process step (2) according to the invention is preferably carried out within a temperature range from −20° C. to +180° C., particularly preferably at temperatures of from −10° C. to +150° C.

Process step (2) according to the invention is generally carried out under atmospheric pressure. Alternatively, however, it is also possible to work under reduced pressure or under superatmospheric pressure (e.g. reaction with phosgene).

The reaction time is not critical and can be selected in a range between a few minutes and several hours depending on the batch size and temperature.

When carrying out the process step according to the invention, 1 mol of the compound of the formula (III) is reacted with 0.1 mol to 2.5 mol, preferably 1 mol to 1.8 mol, particularly preferably with the equimolar amount of the dewatering agent.

If derivatization additionally takes place, 1 mol of the compound of the formula (IV) is reacted with 1 mol to 3 mol, preferably 1.5 mol to 2.5 mol, particularly preferably with 1.8 to 2.5 mol, of the dewatering agent.

It is also possible to eliminate the water catalytically (HCl, $SiO_2$, $H_2SO_4$).

Suitable solvents are, for example, aliphatic, alicyclic or aromatic hydrocarbons, such as e.g. petroleum ether, n-hexane, n-heptane, cyclohexane, methylcyclohexane, benzene, toluene, xylene or decalin, and halogenated hydrocarbons, such as e.g. chlorobenzene, dichlorobenzene, dichloromethane, chloroform, tetrachloromethane, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; ketones, such as acetone, methyl ethyl ketone, methyl isobutyl ketone or cyclohexanone; amides, such as N,N-dimethylformamide, N,N-dimethylacetamide, N-methylformanilide, N-methylpyrrolidone or hexamethylphosphortriamide; sulfoxides, such as dimethyl sulfoxide or sulfones, such as sulfolane. Alcohols such as methanol, ethanol, isopropanol. Particular preference is given to using methanol, methyl tert-butyl ether, toluene, xylene, dichloroethane, dichloromethane, chlorobenzene, cyclohexane or methylcyclohexane, very particularly preferably methanol, toluene, xylene, THF, $CH_2Cl_2$, dichloroethane, methyl tert-butyl ether, acetonitrile. It is also possible to carry out the reaction without solvents, e.g. without dilution.

Furthermore, the aromatization can be carried out under basic conditions (cf. step (2a) in scheme (I)), in order to obtain the compound of the formula (I), in which $R^1$ and $R^2$ are OH, in just one step. Of suitability for this are bases such as, for example LiOH, NaOH, KOH or CsOH. Suitable solvents are alcohols or water.

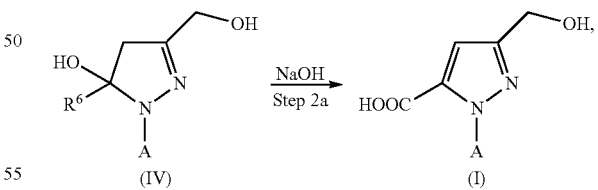

where $R^6$ is (C═O)Oalkyl and A has the meanings given above.

Step 3

In a further preferred embodiment of the process according to the invention, the 1-alkyl-/1-aryl-substituted pyrazoles of the formula (V) are converted directly to the compound of the formula (I) (cf. step 3 in scheme (I)).

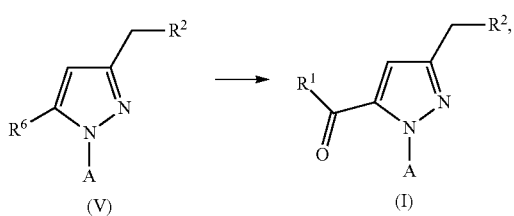

where $R^1$, $R^2$, A, $R^6$ have the meanings given above. Here, the transformations are carried out in the $R^6$ and/or in the $R^2$ group.

For the transformation $R^6$=trihalomethyl to $R^1$=OH, the reaction is generally carried out under acidic or basic conditions. Preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The rate of the reaction can be increased by adding catalysts such as, for example, $FeCl_3$, $AlCl_3$, $BF_3$, $SbCl_3$, $NaH_2PO_4$. The reaction can likewise be carried out just in water without the addition of acid.

Basic hydrolysis takes place in the presence of organic bases such as trialkylamines, alkylpyridines, phosphazenes and 1,8-diazabicyclo[5.4.0]undecene (DBU), inorganic bases such as alkali metal hydroxides, such as e.g. lithium hydroxide, sodium hydroxide or potassium hydroxide, alkali metal carbonates, such as, for example, $Na_2CO_3$, $K_2CO_3$ and alkali metal acetates such as, for example, NaOAc, KOAc, LiOAc, and also alkali metal alcoholates, such as e.g. NaOMe, NaOEt, NaOt-Bu, KOt-Bu.

Process step (3) according to the invention is preferably carried out within a temperature range from 20° C. to +150° C., particularly preferably at temperatures of 30° C. to +110° C.

Process step (3) according to the invention is generally carried out under atmospheric pressure. Alternatively, however, it is also possible to work under reduced pressure or under superatmospheric pressure (e.g. reaction in an autoclave with aqueous HCl, or with methanol).

The reaction time can be selected in a range between 1 hour and several hours depending on the batch size and temperature.

For the transformation $R^6$=trihalomethyl to $R^1$=alkoxy, e.g. alcohols, for example methanol, ethanol, propanol or the combinations alcohol/HCl, alcohol/$FeCl_3$, alcohol/$H_2SO_4$ or alkohol/alcoholate, are used. Here, the alcohol serves as reagent and as solvent at the same time. For the reaction for example with methanol or ethanol, it is advantageous to carry out the reaction under pressure in order to achieve the reaction temperature of 90° or of 90°-100° C. and thus to shorten the reaction time.

Reaction step 3 can be carried out without dilution or in a solvent. The reaction is preferably carried out in a solvent. Suitable solvents are selected for example from the group consisting of water, aliphatic and aromatic hydrocarbons, such as e.g. n-hexane, benzene or toluene, which may be substituted by fluorine and chlorine atoms, such as methylene chloride, dichloroethane, fluorobenzene, chlorobenzene or dichlorobenzene; ethers, such as e.g. diethyl ether, diphenyl ether, methyl tert-butyl ether, isopropyl ethyl ether, dioxane, diglyme, dimethyl glycol, dimethoxyethane (DME) or THF; nitriles such as methylnitrile, butylnitrile or phenylnitrile; amides such as dimethylformamide (DMF) or N-methylpyrollidone (NMP) or mixtures of such solvents, with water, acetonitrile, dichloromethane and alcohols being particularly highly suitable.

PREPARATION EXAMPLES

The preparation examples below illustrate the invention without limiting it. In particular, examples 1, 2, 10, 11 illustrate the preparation of pyrazole compounds of the formula IV (step 1). Examples 7, 12, 13 illustrate step 2. Examples 3, 5, 6 illustrate step 2a and example 9 illustrates step 3.

Example 1

Methyl 1-(3-chloropyridin-2-yl)-5-hydroxy-3-(hydroxymethyl)-4,5-dihydro-1H-pyrazole-5-carboxylate

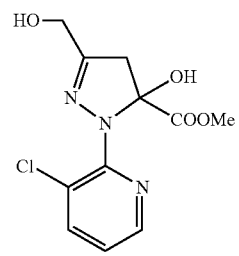 [SMILES: COC(=O)C1(O)CC(CO)=NN1c1ncccc1Cl]

The mixture of methyl 3-(2,2-dimethyl-1,3-dioxolan-4-ylidene)-2-oxopropanoate (20 g, 0.1 mol) and 2-hydrazino-3-chloropyridine (14.3 g, 0.1 mol) in 40 ml of isopropanol was stirred for 18 hours at 35° C. The precipitate was filtered off and washed with 15 ml of isopropanol. This gave 24.2 g (85%) of the product as a pale yellow solid with a melting point of 113° C.

Analytical Characterization $^1$H NMR (DMSO $d_6$) δ: 7.99 (1H, d); 7.65 (1H, d); 6.85 (1H, dd); 6.4 (1H, b.s); 4.51 (2H, b.s); 3.25 (1H, d); 3.05 (1H, d), 2.55 (s, 1H) ppm.

Example 2

Ethyl 1-(3-chloropyridin-2-yl)-5-hydroxy-3-(hydroxymethyl)-4,5-dihydro-1H-pyrazole-5-carboxylate

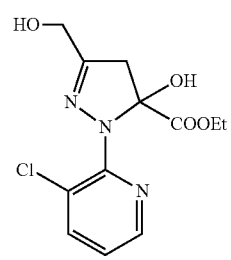 [SMILES: CCOC(=O)C1(O)CC(CO)=NN1c1ncccc1Cl]

The mixture of ethyl (3E)-3-(2,2-dimethyl-1,3-dioxolan-4-ylidene)-2-oxopropanoate (21.4 g, 0.1 mol) and 2-hydrazino-3-chloropyridine (14.3 g, 0.1 mol) in 50 ml of ethanol was stirred for 18 hours at 35° C. Ethanol was removed in vacuo and the residue was taken up in 100 ml of methyl (tert)-butyl ether. The organic phase was washed once with 50 ml of 1% strength HCl and concentrated by evaporation. This gave 26.2 g (86% yield) of the product as a viscous oil with a purity (HPLC) of 97%.

Analytical Characterization $^1$H NMR (DMSO $d_6$) δ: 7.99 (1H, d); 7.65 (1H, d); 6.85 (1H, dd); 6.0 (OH, b.s); 4.51 (2H, b.s); 4.25 (2H, q); 3.25 (1H, d); 3.05 (1H, d), 1.28 (t, 3H) ppm.

Example 3

Methyl 1-(3-chloropyridin-2-yl)-3-(hydroxymethyl)-1H-pyrazole-5-carboxylate

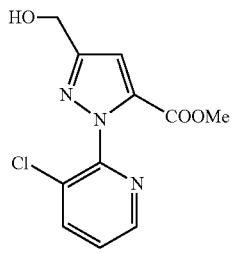 [SMILES: COC(=O)c1cc(CO)nn1-c1ncccc1Cl]

The solution of HCl (9.1 g, 4% solution in methanol) was added to the suspension of (28.5 g, 0.1 mol) of methyl 1-(3-chloropyridin-2-yl)-5-hydroxy-3-(hydroxymethyl)-4,5-dihydro-1H-pyrazole-5-carboxylate in 100 ml of methanol. After ca. 30-60 min at 25-30° C., the clear yellow solution had formed. Methanol was removed in vacuo and the precipitate was washed with water. Yield 26.7 g, 100%. M.p. 104° C.

Analytical Characterization $^1$H NMR (DMSO $d_6$) δ: 8.52 (1H, d); 8.06 (1H, d), 7.55 (1H, dd); 7.10 (1H, s); 5.4 (1H, b.s), 4.5 (2H, s); 3.75 (3H, s) ppm.

Example 4

Methyl 1-(3-chloropyridin-2-yl)-3-(hydroxymethyl)-1H-pyrazole-5-carboxylate

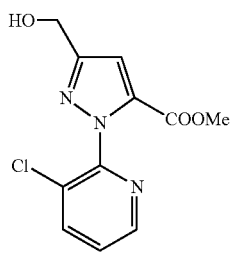 [SMILES: COC(=O)c1cc(CO)nn1-c1ncccc1Cl]

(32.6 g, 0.1 mol) of [1-(3-chloropyridin-2-yl)-5-(trichloromethyl)-1H-pyrazol-3-yl]methanol and 300 ml of methanol were heated in an autoclave for 3 hours at 90° C. Methanol was removed in vacuo and the precipitate was washed with water. Yield 25 g, 88%.

M.p. 104° C.

Example 5

Methyl 1-(3-chloropyridin-2-yl)-3-{[(methylsulfonyl)oxy]methyl}-1H-pyrazole-5-carboxylate

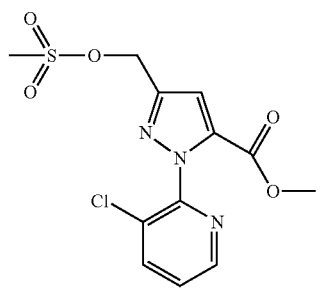

Methyl 1-(3-chloropyridin-2-yl)-5-hydroxy-3-(hydroxymethyl)-4,5-dihydro-1H-pyrazole-5-carboxylate (28.5 g, 0.1 mol) and 15 g of triethylamine were introduced as initial charge in 150 ml of THF and the solution was cooled to 5° C. (11.4 g, 0.1 mol) of mesyl chloride were added at 0-5° C. within 20 min and the mixture was after-stirred at 0° C. for 2 hours. The reaction mixture was diluted with water and the product was extracted with ethyl acetate. The ethyl acetate solution was washed, dried and concentrated by evaporation. The viscous residue (product weight 31 g) contained, according to LC/MS, 98% of the product.

Analytical Characterization $^1$H NMR (DMSO $d_6$) δ: 8.58 (1H, d); 8.27 (1H, d); 7.73 (1H, dd); 7.29 (1H, s); 5.35 (2H, s); 3.75 (3H, q); 3.25 (3H, s) ppm. m/e 345.

Example 6

Methyl 3-(chloromethyl)-1-(3-chloropyridin-2-yl)-1H-pyrazole-5-carboxylate

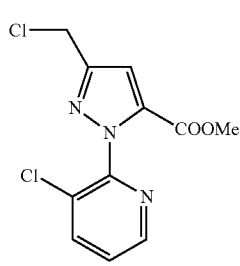 [SMILES: COC(=O)c1cc(CCl)nn1-c1ncccc1Cl]

Methyl 1-(3-chloropyridin-2-yl)-5-hydroxy-3-(hydroxymethyl)-4,5-dihydro-1H-pyrazole-5-carboxylate (28.5 g, 0.1 mol) was dissolved in 100 ml of CH$_3$CN and the solution was heated to 70° C. (26 g, 0.22 mol) of SOCl$_2$ (0.12 mol) was slowly added dropwise at this temperature. The mixture was after-stirred for 1 hour at 70° C. and concentrated by evaporation in vacuo. This gave 27.6 g (92%) of the product as viscous oil with a purity of 95%.

Analytical Characterization $^1$H NMR (CD$_3$CN) δ: 8.52 (1H, d); 8.06 (1H, d), 7.55 (1H, dd); 7.10 (1H, s); 4.75 (2H, s); 3.75 (3H, s) ppm.

Example 7

1-(3-Chloropyridin-2-yl)-5-(trichloromethyl)-1H-pyrazol-3-yl]methyl acetate

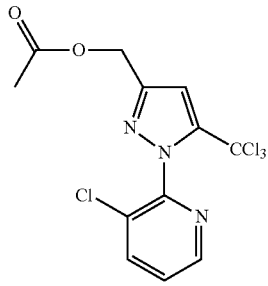

1-(3-Chloropyridin-2-yl)-3-(hydroxymethyl)-5-(trichloromethyl)-4,5-dihydro-1H-pyrazol-5-ol (34.3 g, 0.1 mol) and (12.2 g, 0.12 mol) of acetanhydride were heated at 80° C. for 1 hour and the reaction mixture was completely concentrated by evaporation in vacuo at 1 mbar. This gave 35 g of the product as a viscous oil, which crystallizes after ca. 8 hours at room temperature. M.p. 40° C.

Analytical Characterization $^1$H NMR (DMSO d$_6$) δ: 8.5 (1H, dd); 8.1 (1H, dd); 7.6 (1H, dd); 7.0 (1H, s); 5.1 (2H, dd), 2.0 (3H, s) ppm.

Example 8

[1-(3-Chloropyridin-2-yl)-5-(trichloromethyl)-1H-pyrazol-3-yl]methanol

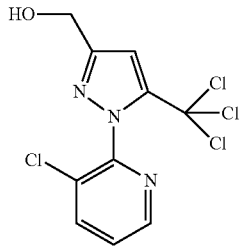 [SMILES: OCc1cc(C(Cl)(Cl)Cl)n(-c2ncccc2Cl)n1]

1-(3-Chloropyridin-2-yl)-5-(trichloromethyl)-1H-pyrazol-3-yl]methyl acetate (36.9 g. 0.1 mol) was dissolved in 100 ml of ethanol, and 10 g of NaOH (as 40% solution in water) were added. After 1 hour, the mixture was diluted with 300 ml of water, and the product was filtered off, washed with water and dried. This gave 31 g (95%) of the product as a white solid.

M.p. 109-111° C.

Analytical Characterization $^1$H NMR (DMSO d$_6$) δ: 8.5 (1H, dd); 8.05 (1H, dd); 7.55 (1H, dd); 6.95 (1H, s); 5.35 (1H, bs); 4.55 (2H, s) ppm.

Example 9

1-(3-chloropyridin-2-yl)-3-(hydroxymethyl)-1H-pyrazole-5-carboxylic acid

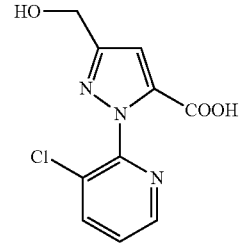 [SMILES: O=C(O)c1cc(CO)nn1-c1ncccc1Cl]

38.7 g (0.1 mol) of [1-(3-chloropyridin-2-yl)-5-(trichloromethyl)-1H-pyrazol-3-yl]methanol and 10 g of H$_2$SO$_4$ (as 10% solution in water) were stirred for 3 hours at 80° C. The mixture was cooled to 0° C., made neutral with NaHCO$_3$ solution and the precipitate was filtered off, washed with acetonitrile and dried. Yield 90%. M.p. 178-180° C.

Analytical Characterization $^1$H NMR (DMSO d$_6$) δ: 12.8 (1H, b.s); 8.45 (1H, dd); 8.1 (1H, dd); 7.55 (1H, dd); 6.95 (1H, s); 5.2 (1H, b.s); 4.50 (2H, s) ppm.

Example 10

3-(Hydroxymethyl)-1-phenyl-5-(trifluoromethyl)-4,5-dihydro-1H-pyrazol-5-ol

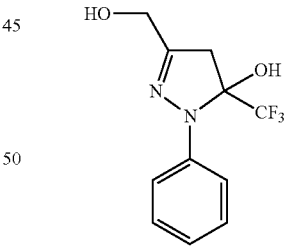

The procedure is as described in example 1, but using phenylhydrazine and 1,1,1-trifluoro-3-(2,2-dimethyl-1,3-dioxolan-4-ylidene)acetone.

Yield (62%), M.p. 72-74° C.

Analytical Characterization $^1$H NMR (DMSO-d$_6$) δ: 7.98 (1H, b.s); 7.32 (2H, m), 7.24 (2H, m), 6.94 (1H, m), 5.50-5.00 (1H, b.s), 4.20 (2H, s, CH$_2$OH), 3.43 and 3.21 (2H, AB system, J$_{HH}$=19.1 Hz, CH$_2$) ppm.

Example 11

3-(Hydroxymethyl)-1-phenyl-5-(trichloromethyl)-4,5-dihydro-1H-pyrazol-5-ol

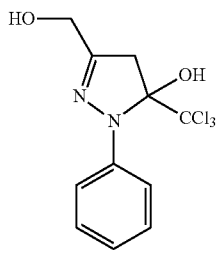

The procedure is as described in example 2 but using phenylhydrazine and 1,1,1-trichloro-3-(2,2-dimethyl-1,3-dioxolan-4-ylidene)acetone.

Yield (68%), M.p. 122-124° C. (decomposition).

Analytical Characterization $^1$H NMR (DMSO-d$_6$) δ: 8.17 (1H, b.s), 7.49 (2H, m), 7.21 (2H, m), 6.96 (1H, m), 4.70-4.30 (1H, b.s), 4.18 (2H, s), 3.64 and 3.34 (2H, AB system, J$_{HH}$=19.3 Hz, CH$_2$) ppm.

Example 12

(1-Phenyl-5-(trifluoromethyl)-1H-pyrazol-3-yl)methanol

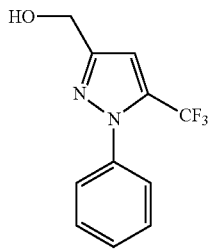 [SMILES: OCc1cc(C(F)(F)F)n(-c2ccccc2)n1]

3-(Hydroxymethyl)-1-phenyl-5-(trifluoromethyl)-4,5-dihydro-1H-pyrazol-5-ol (5 g) was heated at 100-120° C. for 30 min. The product was isolated and purified by means of column chromatography (eluent: ethyl acetate:hexane 1/1 mixture), yield 1.5 g (32%).

Analytical Characterization $^1$H NMR (CDCl$_3$) δ: 7.46 (5H, m), 6.80 (1H, s), 4.73 (2H, s), 2.50 (1H, br. s);

$^{19}$F NMR (CDCl$_3$) δ: −58.16 (s, CF$_3$) ppm.

Example 13

1-Phenyl-5-(trichloromethyl)-1H-pyrazol-3-yl)methanol

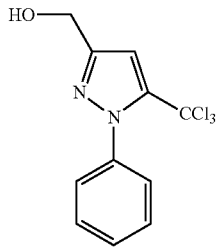

The procedure is as described in example 12 but using 3-(hydroxymethyl)-1-phenyl-5-(trichloromethyl)-4,5-dihydro-1H-pyrazol-5-ol.

Yield 21%.

Analytical Characterization $^1$H NMR (CDCl$_3$) δ: 7.6-7.5 (5H, m), 7.00 (1H, br. s), 4.74 (2H, s), 2.47 (1H, b.s) ppm.

Furthermore, in particular, Preparation Examples 14, 15, 16 and 17 illustrate the preparation of intermediates of the formula (VII), (step 1a) of the further embodiment of the process according to the invention, and Examples 18, 19, 20 and 21 illustrate the preparation of pyrazole compounds of the formula (IV) (step 1b).

Example 14

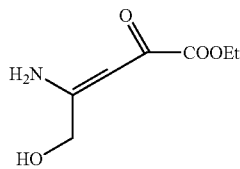 [SMILES: CCOC(=O)C(=O)C=C(N)CO]

(Z)- and (E)-ethyl 4-amino-5-hydroxy-2-oxopent-3-enoate

A solution of (6 g, 28 mmol) of (E)-ethyl 3-(1,3-dioxolan-4-ylidene)-2-oxopropanoate in 25 ml of acetonitrile was admixed with 2.7 ml (28 mmol) of ammonia (as a 19% solution in water).

The reaction mixture was subsequently stirred at 25° C. for 3 hours and concentrated under reduced pressure. The residue was washed with hexane. This gave 3.8 g (78.4%).

$^1$H NMR (DMSO-d$_6$) δ: cis-isomer (~90%): 9.89 (1H, b.s, NH), 8.28 (1H, b.s, 1H, NH), 5.66 (1H, s, CH), 5.61 (1H, b.s, OH), 4.15 (2H, q, OCH$_2$), 4.14 (2H, s, CH$_2$), 1.22 (3H, t, CH$_3$); trans-isomer (~10%): 8.37 (1H, b. s, NH), 7.11 (1H, b. s, NH), 5.75 (1H, s, CH), 4.57 (2H, s, CH$_2$).

Example 15

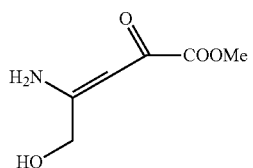 [SMILES: COC(=O)C(=O)C=C(N)CO]

(Z)- and (E)-methyl 4-amino-5-hydroxy-2-oxopent-3-enoate

A solution of (9 g, 45 mmol) of methyl (3E)-3-(2,2-dimethyl-1,3-dioxolan-4-ylidene)-2-oxopropanoate in 50 ml of acetonitrile was admixed with ammonia solution (2.32 g, 45 mmol, 33% solution in water). After about 2 hours, the white solid was isolated by filtration with suction, and washed with cold acetonitrile. This gave 5.36 g (75%) of the product, with melting point 130-132° C.

$^1$H NMR (DMSO-d$_6$) δ: cis-isomer (95%): 9.91 (1H, b.s, NH), 8.35 (1H, b.s, NH), 5.68 (1H, s), 5.67 (1H, b.s, 1H, OH), 4.15 (2H, s), 3.7 (3H, s), trans-isomer (~5%): 8.36 (1H, b. s, NH), 7.12 (1H, b.s, NH), 5.76 (1H, s, CH), 4.15 (2H, s), 3.68 (3H, s) ppm.

Example 16

5-Hydroxy-5-(trifluoromethyl)dihydrofuran-3-(2H)-one

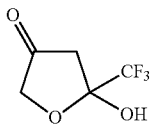

A mixture of 3-(2,2-dimethyl-1,3-dioxolan-4-ylidene)-1,1,1-trifluoroacetone (5.21 g, 24.8 mmol) and 20 ml water was stirred at 20° C. for 24 hours. The volatile components were removed under a reduced pressure of 20 mbar. The product was extracted with dichloromethane and the organic phase was dried over MgSO$_4$ and concentrated. The precipitate was purified by crystallization from toluene.

Yield: 3.0 g (71.1%), m.p. 45-47° C.

$^1$H NMR (DMSO-d$_6$) δ: 8.08 (1H, s), 4.28 (2H, m), 3.05 and 2.65 (AB system, CH$_2$, J$_{HH}$=18.2 Hz) ppm.

$^{19}$F NMR (DMSO-d$_6$) −85.24 (s) ppm.

Example 17

Ethyl 2-hydroxy-4-oxotetrahydrofuran-2-carboxylate

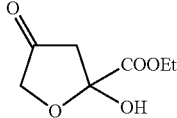

The procedure described in Example 16 is repeated, but taking ethyl 3-(2,2-dimethyl-1,3-dioxolan-4-ylidene)-2-oxopropanoate.

Yield 77%.

$^1$H NMR (CDCl$_3$) δ: 4.62 (1H, b.s), 4.28 (2H, q), 4.22 and 4.12 (AB system, J$_{HH}$=16.6 Hz) 3.05 and 2.59 (AB system, J$_{HH}$=18.3 Hz), 1.30 (3H, t) ppm.

Example 18

Preparation of methyl 1-(3-chloropyridin-2-yl)-5-hydroxy-3-(hydroxymethyl)-4,5-dihydro-1H-pyrazole-5-carboxylate via methyl 2-hydroxy-4-oxotetrahydrofuran-2-carboxylate

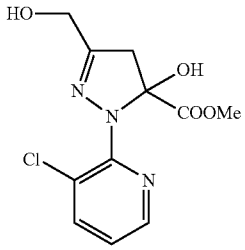 [SMILES: COC(=O)C1(O)CC(CO)=NN1c1ncccc1Cl]

2 g (10 mmol) of methyl 3-(2,2-dimethyl-1,3-dioxolan-4-ylidene)-2-oxopropanoate and 20 ml of water were stirred at RT for 18 hours. The precipitate goes into the solution. The solution was stirred under a reduced pressure of 100 mbar for 1 hour, during which about 10 ml of the liquid were removed. 10 ml of isopropanol and (1.43 g, 10 mmol) of 3-chloropyridin-2-ylhydrazine were added, and the mixture was subsequently stirred at RT for 24 hours. The precipitate was isolated by filtration and washed with isopropanol. This gave 2.1 g (74%) of the product, with a melting point of 111-113° C.

Example 19

Ethyl 1-(3-chloropyridin-2-yl)-5-hydroxy-3-(hydroxymethyl)-4,5-dihydro-1H-pyrazole-5-carboxylate

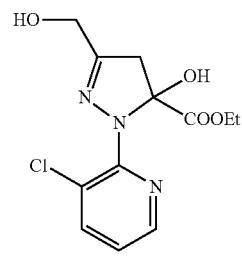 [SMILES: CCOC(=O)C1(O)CC(CO)=NN1c1ncccc1Cl]

A mixture of ethyl 4-amino-5-hydroxy-2-oxopent-3-enoate (2.5 g, 14 mmol), 3-chloropyridin-2-ylhydrazine (2.07 g, 14 mmol) and p-toluenesulphonic acid monohydrate (2.5 g, 13 mmol) was stirred in 25 ml of acetonitrile at 25° C. for 5 hours. The precipitate was isolated by filtration and the filtrate was concentrated under reduced pressure. The product was purified by column chromatography on SiO$_2$ (eluent: hexane/ethyl acetate). Oil. Yield 4.2 g (90%).

$^1$H NMR (DMSO-d$_6$) δ: 8.02 (1H, m), 7.78 (1H, m), 6.88 (1H, m), 5.60 (1H, b. s), 5.29 (1H, b. s), 4.24 (2H, s), 4.13 (2H, q), 3.18 and 2.94 (2H, AB system, J$_{HH}$=17.9 Hz), 1.08 (3H, t) ppm.

Example 20

Methyl 1-(3-chloropyridin-2-yl)-5-hydroxy-3-(hydroxymethyl)-4,5-dihydro-1H-pyrazole-5-carboxylate

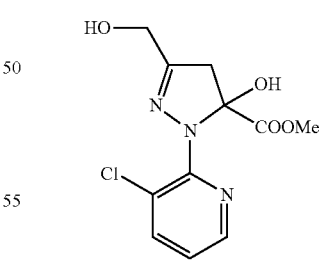

A mixture of methyl 4-amino-5-hydroxy-2-oxopent-3-enoate (1.59 g, 10 mmol), 3-chloropyridin-2-ylhydrazine (1.43 g, 10 mmol and HCl (1 g, 10 mmol, 37% solution in water) was stirred in 15 ml of acetonitrile at 25° C. for 20 hours. The solution was concentrated under reduced pressure and the residue was washed with water and isopropanol. This gave 2.13 g (75%) of the product, with a melting point of 111-113° C.

Analytical Characterization $^1$H NMR (DMSO-d$_6$) δ: 7.99 (1H, d); 7.65 (1H, d); 6.85 (1H, dd); 6.4 (1H, b.s); 4.51 (2H, b.s); 3.25 (1H, d); 3.05 (1H, d), 2.55 (s, 1H) ppm.

Example 21

Ethyl 1-(3-chloropyridin-2-yl)-3-(hydroxymethyl)-1H-pyrazole-5-carboxylate

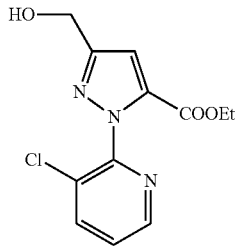 [SMILES: CCOC(=O)c1cc(CO)nn1-c1ncccc1Cl]

The procedure described in Example 3 is repeated, but using ethyl 1-(3-chloropyridin-2-yl)-5-hydroxy-3-(hydroxymethyl)-4,5-dihydro-1H-pyrazole-5-carboxylate.

Yield 98%. Viscous oil.

$^1$H NMR (DMSO-d$_6$) δ: 8.56 (1H, m), 8.24 (1H, m), 7.68 (1H, m), 7.07 (1H, s), 5.39 (1H, b. s), 4.54 (2H, s), 4.14 (2H, q), 1.09 (3H, t) ppm.

The invention claimed is:

1. A process for the preparation of a compound of formula (I)

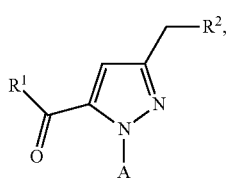

in which
R$^1$ is hydroxy, halogen, alkoxy, or aryloxy,
R$^2$ is hydroxy, alkoxy, arylalkoxy, halogen, O—(C═O)alkyl, O—(C═O)O-alkyl, O(C═O)haloalkyl, OSO$_2$alkyl, OSO$_2$-haloalkyl, or OSO$_2$-aryl,
A is alkyl or
is

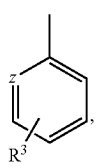

in which
R$^3$ is halogen, CN, NO$_2$, alkyl, cycloalkyl, haloalkyl, halocycloalkyl, alkoxy, haloalkoxy, alkylamino, dialkylamino, or cycloalkylamino, and Z is CH or N,
comprising, reacting a compound of formula (II)

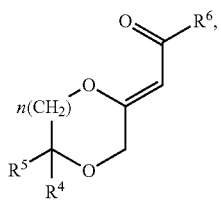

in which
R$^4$ and R$^5$ independently of one another are hydrogen, alkyl, aryl, arylalkyl, or alkoxy, or
R$^4$ and R$^5$ taken together can form a 4-, 5- or 6-membered, saturated, optionally substituted ring which can contain 1-2 heteroatoms from the series N, S, O,
R$^6$ is trihalomethyl, (C═O)Oalkyl, or (C═O)Ohaloalkyl,
n is 0 or 1,
with an alkyl- or arylhydrazine of formula (III)

A-NHNH$_2$     (III), in which A is alkyl or is

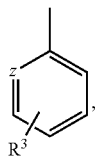

in which
R$^3$ is halogen, CN, NO$_2$, alkyl, cycloalkyl, haloalkyl, halocycloalkyl, alkoxy, haloalkoxy, alkylamino, dialkylamino, or cycloalkylamino,
Z is CH or N,
in the presence of a solvent to obtain a compound of formula (IV),

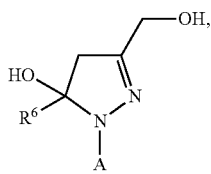

in which R$^6$ and A are defined above,
wherein said compound of formula (IV) is optionally further reacted without prior isolation with elimination of water, in the presence of a solvent, to obtain a compound of formula (V)

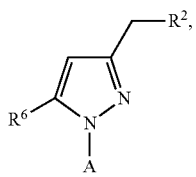

in which R$^2$, R$^6$ and A are defined above, wherein said compound
of formula (V)

is reacted in the presence of a solvent to obtain a compound of formula (I),

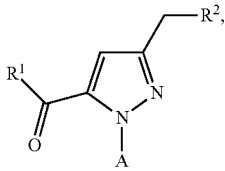

in which $R^1$, $R^2$ and A are defined above.

2. The process according to claim 1, where
$R^1$ is hydroxy, halogen, or $(C_1-C_6)$alkoxy,
$R^2$ is hydroxy, halogen, O—(C=O) $(C_1-C_6)$alkyl, $OSO_2$ $(C_1-C_6)$alkyl, or $OSO_2$-halo$(C_1-C_6)$alkyl, and
A is $(C_1-C_4)$alkyl or
is

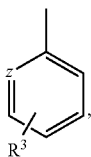

in which
$R^3$ is halogen, CN, $NO_2$, $(C_1-C_6)$-alkyl, halo$(C_1-C_6)$-alkyl, or $(C_1-C_6)$alkoxy, halo$(C_1-C_6)$alkoxy, and
Z is N.

3. The process according to claim 1, where
$R^1$ is hydroxy, halogen, or $(C_1-C_4)$alkoxy,
$R^2$ is hydroxy, halogen, or, O—(C=O)$CH_3$, and
A is

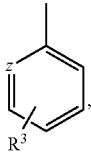

in which
$R^3$ is chlorine, and
Z is N.

4. The process according to claim 1, wherein n is 0.

5. The process according to claim 1 comprising, reacting said compound of formula (II)

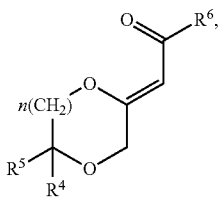

in which n is 0 and $R^4$, $R^5$ and $R^6$ are defined above, with a nucleophile of formula (VI)

$H_2L$         (VI), in which L is O, NH or $NR^7$,
$R^7$ is alkyl,
to give a product, wherein said product is present in tautomeric forms (VIIa) and (VIIb), wherein said tautomeric forms, optionally form a ring of formula (VIIc), or (VIId), or a combination thereof:

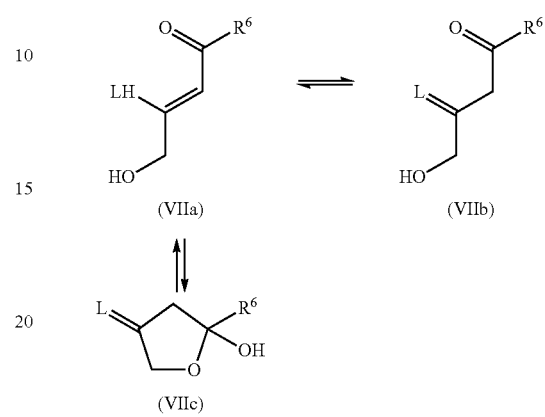

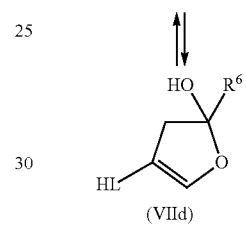

wherein said product is subsequently reacted with a compound of formula (III)

A-NHNH₂         (III), in which A is defined above,
to give said compound of formula (IV),

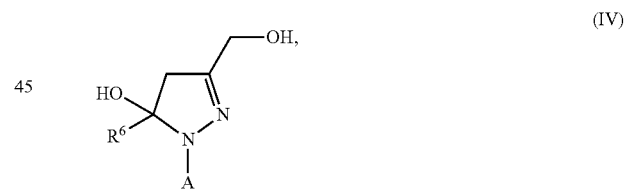

in which A and $R^6$ are defined above.

6. The process according to claim 1, wherein said reaction of said compound of formula (II) with said compound of formula (III) is carried out within a temperature range from −20° C. to +100° C.

7. The process according to claim 1, wherein 1 mol of said compound of formula (II) is reacted with 0.8 mol to 2 mol of said compound of formula (III).

8. The process according to claim 1 wherein, the compound of formula (IV) is reacted, with addition of a base, directly to obtain the compound of formula (I), where
$R^1$ and $R^2$ are hydroxy, $R^6$ is (C=O)Oalkyl, and
$R^3$, $R^4$, $R^5$, A and Z are defined as in claim 1.

9. The process according to claim 8, further comprising using an alcohol or water as solvents, wherein the base is selected from the group consisting of LiOH, NaOH, KOH and CsOH.

10. The process according to claim 1, wherein said reaction of said compound of formula (V) to obtain said compound of formula (I) is carried out within a temperature range from 20° C. to +150° C.

11. The process according to claim 1, wherein said reaction of said compound of formula (V) to obtain said compound of formula (I) is carried out under acidic conditions with mineral or organic acids or under basic conditions with organic or inorganic bases.

12. The process according to claim 10, wherein said reaction carried out with alcohol, or alcohol/HCl, alcohol/FeCl$_3$, alcohol/H$_2$SO$_4$ or alcohol/alcoholate or combinations thereof.

13. The process according to claim 1, wherein the compound of formula (IV) is reacted, with the addition of an acid (HCl), to obtain the compound of formula (I), where
$R^1$ is (C=O)Oalkyl, $R^2$ is hydroxy and $R^6$ is (C=O)Oalkyl, and
$R^3$, $R^4$, $R^5$, A and Z are defined as in claim 1.

14. The process according to claim 10 wherein said reaction is carried out under acidic conditions with mineral or organic acids or under basic conditions with organic or inorganic bases.

15. The process according to claim 1, wherein reaction of said compound of formula (V) to obtain said compound of formula (I) is carried out with alcohol, or alcohol/HCl, alcohol/FeCl$_3$, alcohol/H$_2$SO$_4$ and alcohol/alcoholate, or combinations thereof.

* * * * *